United States Patent [19]

Imi et al.

[11] Patent Number: 5,945,563
[45] Date of Patent: Aug. 31, 1999

[54] PROCESS FOR PRODUCING METHIONINE

[75] Inventors: Katsuharu Imi, Niihama; Tetsuya Shiozaki, Saijo, both of Japan

[73] Assignee: Sumitomo Chemical Company, Limited, Osaka, Japan

[21] Appl. No.: 08/958,335

[22] Filed: Oct. 27, 1997

[30] Foreign Application Priority Data

Oct. 31, 1996 [JP] Japan .................................. 8-290090

[51] Int. Cl.$^6$ ................................................ C07C 321/00
[52] U.S. Cl. ............................................................ 562/559
[58] Field of Search ............................................. 562/559

[56] References Cited

U.S. PATENT DOCUMENTS 4,069,251 1/1978 Mannsfeld et al. .
4,272,631 6/1981 Schaaf et al. ............................ 562/559
4,303,621 12/1981 Lussling et al. .

FOREIGN PATENT DOCUMENTS 05320124 12/1993 Japan .

Primary Examiner—Paul J. Killos
Assistant Examiner—J. Parsa
Attorney, Agent, or Firm—Stevens, Davis, Miller & Mosher, L.L.P.

[57] ABSTRACT

Methionine is produced in an improved yield while reducing the load of waste water disposal by a process including the steps of:

(A) adding at least one compound selected from potassium carbonate, potassium bicarbonate and potassium hydroxide to a solution containing 5-(β-methylmercaptoethyl)hydantoin, (B) saturating the resulting solution with carbon dioxide gas and separating deposited methionine while leaving a first filtrate behind, (C) transferring part or whole of the first filtrate to step (D), (D) heating the transferred filtrate, adding a water-miscible solvent to it and saturating it with carbon dioxide gas to deposit methionine and potassium bicarbonate, and separating these deposits while leaving a second filtrate behind, and (E) returning the second filtrate to step (A) if desired.

7 Claims, No Drawings

PROCESS FOR PRODUCING METHIONINE

The present invention relates to a process for producing methionine, a useful livestock feed additive. In more particular the invention relates to a process for producing methionine from 5-(β-methylmercaptoethyl)-hydantoin while recovering methionine and potassium bicarbonate from a filtrate from which methionine has been separated and collected by a conventional method.

U.S. Pat. No. 4,069,251 discloses a continuous process for the production of methionine comprising the steps of hydrolyzing 5-(β-methylmercaptoethyl)hydantoin in an aqueous solution of alkali carbonate and/or alkali bicarbonate, and separating the produced methionine by means of carbon dioxide while the mother liquor containing the alkali bicarbonate is recirculated into the process.

Since the mother liquor is recirculated into the process, it is necessary to remove a definite portion of the mother liquor to the outside of the system, in other words, to conduct the so-called partial purging, in order to avoid the accumulation of impurities and colored components in the system. However, since the mother liquor removed by partial purging, namely the partly purged liquid, still contains methionine and potassium, which are valuable components, it is disadvantageous from the viewpoints of economy and environmental-friendliness to discard the partly purged liquid as it is untreated. Therefore, the aforesaid reference suggests saturating a fraction of the mother liquor at as low as temperature as possible with carbon dioxide in order to separate out the formed methionine and bicarbonate and reacting it with twice or three times amount of a water-soluble solvent such as methanol and acetone.

U.S. Pat. No. 4,303,621 discloses that methionine and potassium can be recovered from the recycling solutions of the potassium carbonate-methionine process by carbonation in an easily filterable form if the mother liquors resulting after the separation of the main amount of methionine are concentrated and carbonated with cooling, that the mother liquors are concentrated to a concentration of at least 120 grams of titratable potassium per liter, and that the carbonation occurs at carbon dioxide pressures of 0.5–20 atmospheres absolute.

JP-A-5-320124 discloses a process for producing methionine which comprises separating and collecting methionine from a mother liquor to leave a filtrate behind, adding isopropyl alcohol to the filtrate in an amount of 0.5–2 parts by weight per part by weight of the filtrate, saturating the filtrate with carbon dioxide at a pressure of 0.5–20 kg/cm$^2$G under cooling to deposit methionine and potassium bicarbonate, and separating and recovering these deposits.

According to these processes, however, methionine dimer existing together with methionine cannot be deposited and are left in the mother liquor or in the filtrate. Methionine dimer is converted by hydrolysis into methionine when the mother liquor or filtrate is recycled to the step of hydrolysis of 5-(β-methylmercapto)hydantoin and hence is to be regarded as an equivalent of methionine. In the conventional processes described above, the methionine dimer contained in the partly purged liquid is discarded without being recovered, which results in the problems of lowering of the yield of methionine and increasing the load in waste water disposal.

To solve such problems, the present inventors have made extensive study to find an effective method of recovering methionine dimer in the mother liquor or filtrate. As the result, it has been found that the methionine dimer can be effectively utilized and resultantly the yield of methionine can be improved and the load of waste water can be greatly decreased by heat-treating the filtrate obtained after separation and collection of methionine to hydrolyze methionine dimer into methionine, then adding a water-miscible solvent to the heat-treated filtrate and saturating the heat-treated filtrate with carbon dioxide gas to deposit methionine and potassium bicarbonate, and separating and collecting them. The present invention has been accomplished on the basis of the above finding.

According to the present invention, there is provided a process for producing methionine which comprises the steps of:

(A) adding at least one compound selected from potassium carbonate, potassium bicarbonate and potassium hydroxide to a solution containing 5-(β-methylmercaptoethyl)hydantoin to hydrolyze the 5-(β-methylmercaptoethyl)hydantoin to obtain a solution containing methionine, (B) saturating the solution containing methionine with carbon dioxide gas to deposit the methionine, and separating the deposited methionine while leaving a first filtrate behind, (C) dividing the first filtrate into a first part and a second part, returning the first part to step (A), and transferring the second part to step (D), wherein the first part of the first filtrate can be absent, (D) heating the second part of the first filtrate to obtain a heat-treated filtrate, adding a water-miscible solvent to the heat-treated filtrate and saturating the heat-treated filtrate with carbon dioxide gas to deposit the methionine and potassium bicarbonate, and separating the deposited methionine and potassium bicarbonate while leaving a second filtrate behind, and (E) discharging the second filtrate or returning it to step (A).

The present invention is to be applied to a process for producing methionine which comprises hydrolyzing 5-(β-methylmercaptoethyl)hydantoin by using at least one member selected from potassium carbonate, potassium bicarbonate and potassium hydroxide, then depositing methionine out of the reaction liquid under applied pressure of carbon dioxide gas, separating and collecting the methionine to leave a filtrate, and recycling, for reusing, the filtrate to the step of the hydrolysis of the hydantoin compound. The invention is characterized, in adding a water-miscible solvent to a part or the whole of the filtrate which is recycled, for reusing, to the step of the hydrolysis of the hydantoin compound, crystallizing methionine and potassium bicarbonate from the filtrate under applied pressure of carbon dioxide gas, and separating and recovering them, by first heat-treating the filtrate, then adding a water-miscible solvent to the heat-treated filtrate, crystallizing methionine and potassium bicarbonate out of the heat-treated filtrate under applied pressure of carbon dioxide gas, and separating and recovering them.

In the present invention, the conditions for the above-mentioned steps (A) and (B) are not particularly limited. As to the conditions for steps (A) and (B), known methods, for example as described in U.S. Pat. No. 4,069,251 and U.S. Pat. No. 4,303,621, can be used. In such a method, 5-(β-methylmercaptoethyl)hydantoin is hydrolyzed by using potassium carbonate and/or potassium bicarbonate, the ratio between the hydantoin and the alkali (potassium carbonate and/or potassium bicarbonate) possibly being between 1:1 and 1:5, at an approximate temperature of from 120° to 220° C., then carbon dioxide gas is fed to the reaction system to saturate the methionine-containing solution and thereby to deposit methionine, and the methionine thus deposited is separated by conventional methods of solid-liquid separation.

In the present invention, part of the first filtrate left behind in step (B) can be returned to the circulatory system as it is or after it is concentrated, and recycled to and reused in step (A). Recycling and reusing all the filtrate in this way over a long period would undesirably accumulate impurities and decomposition products in the system, whereby would frequently reduce the purity of methionine produced. Therefore, in order to avoid the potential risk of accumulation of impurities and colored components in the system, it has been recommended to remove the filtrate according to necessity, for example in a definite proportion, out of the system (the so-called partial purging).

In the present invention, the second filtrate left behind in step (D) can be returned to step (A), although it can be discharged economically and environmental-friendly.

In the present invention, the amount of the filtrate to be partly purged (second part of the first filtrate in step (C)) is not particularly limited and may vary depending on the amounts of impurities and colored substances contained in the first filtrate, but it is preferably about 5–20% of the total amount of the first part of the first filtrate if it is present and the second filtrate if it is recycled and reused. The second part of the first filtrate can be heat-treated as it is or after it is concentrated. The filtrate to be heat-treated usually contains about 90–160 g/l of potassium, about 30–60 g/l of methionine and about 5–25 g/l of methionine dimer. The concentration of potassium referred to in the present invention may be determined by titration.

The temperature of the heat treatment of the second part of the first filtrate is not particularly limited and may vary depending on the concentration of methionine dimer contained therein. It preferably falls within an approximate range of 150°–200° C., more preferably within an approximate range of 170°–190° C. The hydrolysis of the dimer proceeds slowly at lower temperatures. The dimer can be rapidly hydrolyzed at a temperature higher than 200° C., but the methionine may be suffered from thermal degradation and moreover the corrosion of materials of reaction equipment is apt to occur.

The period of time for heat treatment also is not particularly limited and may vary depending on the concentration of methionine dimer in the second part of the first filtrate. It is preferably about 0.3 hour to about 10 hours, more preferably about 1 hour to about 3 hours. The dimer may not be completely hydrolyzed within a short time of heat treatment. A long period of time of heat treatment permits complete hydrolysis of the dimer, but the methionine may be suffered from thermal degradation and moreover the corrosion of materials of reaction equipment is apt to occur.

In the present invention, a water-miscible solvent is added to the heat-treated filtrate either as it is or after concentration, and the heat-treated filtrate is saturated with carbon dioxide gas to deposit methionine and potassium bicarbonate, which are then separated and recovered. There is no particular order between the water-miscible solvent adding operation and the carbon dioxide gas saturating operation, and both operations can be conducted at the same time. The usable water-miscible solvents include alcohols, such as isopropyl alcohol and methanol, and acetone.

The person skilled in the art would be able to determine the amount of water-miscible solvent to be added with ordinary experimentations. The amount usually ranges from about 0.2 to about 2 parts by weight relative to 1 part by weight of the heat-treated filtrate as it is or the heat-treated filtrate after concentration. When the amount of the water-miscible solvent is less than 0.2 part by weight per 1 part by weight of the filtrate, the recoveries of methionine and potassium bicarbonate tend to be low; on the other hand, even when the amount is increased over about 2 parts by weight, the recoveries of methionine and potassium carbonate may not be improved in proportion to the increase in the amount.

The pressure of carbon dioxide gas to be applied, in terms of gauge pressure (the amount by which the total absolute pressure exceeds the ambient atmospheric pressure), is not critical, but usually ranges from about 0.5–20 kg/cm$^2$, preferably about 2–6 kg/cm$^2$. When the pressure of carbon dioxide gas is less than about 0.5 kg/cm$^2$ G the recoveries of methionine and potassium bicarbonate tend to be insufficient irrespective of the amount of the water-miscible solvent used; on the other hand, even when the pressure is increased over about 20 kg/cm$^2$ G, sometimes no further improvement in these recoveries is observed.

The deposition is preferably carried out at low temperatures. The deposition temperature, particularly at the time of completion of the deposition, preferably falls within the range of from about $-10°$ C. to about $+40°$ C., more preferably from about $0°$ C. to about $+20°$ C., still more preferably in the neighborhood of about $+10°$ C.

In the present invention, a concentrating operation can be conducted in any step, and is preferably conducted before and/or after the heat treatment of the second part of the first filtrate. The conditions of the concentrating operation are not particularly limited so long as they do not cause substantial thermal degradation of methionine, therefore, various conditions may be adopted in principle. However, in consideration of the energy efficiency and the corrosion of the materials of the reaction equipment, the temperature of the concentrating operation preferably falls within the range of from about $50°$ C. to about $160°$ C., more preferably from about $50°$ C. to about $140°$ C., and the pressure of the concentrating operation preferably falls within the range of from 0 to about 2 kg/cm$^2$ in terms of gauge pressure or a reduced pressure, more preferably from 0 to about 1.5 kg/cm$^2$ in terms of gauge pressure. In the present invention, the concentrating operation can be conducted simultaneously in combination with the heat-treating operation in step (D). In such a case, the concentrating operation would naturally be conducted under the above-mentioned operation conditions of heat treatment. However, it would not be preferable from the viewpoint of energy efficiency and other factors to adopt the relatively severe operation conditions in heat treatment for the purpose of concentrating operation. Therefore, the concentrating operation and the heat-treating operation are preferably conducted independently of each other.

According to the present invention, treating the second part of the first filtrate in the manner described above enables to remove the impurities and colored components present in the circulatory system off to the outside of the system while effectively recovering methionine and potassium bicarbonate contained in the filtrate.

Step (D) of treating second part of the first filtrate in the present invention can be conducted either batchwise or continuously.

Step (E) can be conducted after recovering the water-miscible solvent from the second filtrate.

As described above, according to the present invention, merely by using a method which comprises heat-treating the second part of the first filtrate taken from the conventional process for producing methionine, then adding a water-miscible solvent to the heat-treated filtrate, and depositing methionine out of the heat-treated filtrate under applied pressure of carbon dioxide gas, methionine dimer present in the system can be utilized effectively and resultantly the yield of methionine is improved, the load of waste water is greatly decreased, the increase of impurities and colored substances in the reaction system is avoided, and methionine and potassium bicarbonate can be recovered easily and with good efficiency. Thus, the present invention is of a great industrial value.

The present invention is described in detail below with reference to Examples and Comparative Examples, but the invention is not limited thereto.

EXAMPLE 1

In a 1-l stainless steel autoclave was placed a filtrate containing 100 g/l of potassium, 50 g/l of methionine and 20 g/l of methionine dimer. The filtrate was heated at a predetermined temperature shown in Table 1. Samples of the filtrate were taken at intervals with the lapse of time and the content of methionine dimer in the filtrate sample was determined by means of liquid chromatography. Then the hydrolysis rate of methionine dimer was calculated according to the following equation. The results thus obtained are shown in Table 1.

Hydrolysis rate (%) of methionine dimer =

$$\frac{\left(\begin{array}{c}\text{Methionine dimer}\\\text{content before heating}\end{array}\right) - \left(\begin{array}{c}\text{Mehtionine dimer}\\\text{content after heating}\end{array}\right)}{\text{Methionine dimer content before heating}} \times 100$$

TABLE 1

| Heating temperature | Methionine dimer hydrolysis rate after the lapse of heating time shown below | | | |
|---|---|---|---|---|
|  | 0.5 hr | 1 hr | 2 hr | 3 hr |
| 160° C. | 13% | 18% | 31% | 42% |
| 170° C. | 23% | 35% | 54% | 69% |
| 180° C. | 42% | 58% | 78% | 88% |
| 190° C. | 59% | 76% | 90% | 94% |
| 200° C. | 73% | 86% | 96% | 98% |

EXAMPLE 2

In a 1-l stainless steel autoclave was placed a filtrate containing 145 g/l of potassium, 50 g/l of methionine and 20 g/l of methionine dimer, and the filtrate was heated at a predetermined temperature shown in Table 2. Samples of the filtrate were taken at intervals with the lapse of time and the content of methionine dimer in the filtrate sample was determined by means of liquid chromatography, from which the hydrolysis rate of methionine dimer was calculated. The results thus obtained are shown in Table 2.

TABLE 2

| Heating temperature | Methionine dimer hydrolysis rate after the lapse of heating time shown below | | | |
|---|---|---|---|---|
|  | 0.5 hr | 1 hr | 2 hr | 3 hr |
| 170° C. | 22% | 34% | 54% | 68% |
| 180° C. | 51% | 70% | 87% | 92% |

EXAMPLE 3

Into a stainless steel reaction pipe (8 cm in diameter, 134 cm in length, temperature being set as shown in Table 3) covered with a heat insulating material was continuously introduced a filtrate containing 145 g/l of potassium, 50 g/l of methionine and 20 g/l of methylene dimer which had been preheated immediately before the introduction. The filtrate was continuously withdrawn after a retention time of 1 hour. The withdrawn filtrate was cooled immediately and analyzed for the content of methionine dimer therein by means of liquid chromatography to determine the hydrolysis rate of the dimer. The results thus obtained are shown in Table 3.

TABLE 3

| Reaction pipe inlet temperature | Reaction pipe outlet temperature | Methionine dimer hydrolysis rate |
|---|---|---|
| 155–167° C. | 144–150° C. | 13% |
| 154–170° C. | 147–156° C. | 17% |
| 164–178° C. | 153–160° C. | 26% |
| 176–188° C. | 169–174° C. | 35% |
| 184–198° C. | 173–181° C. | 39% |

EXAMPLE 4

In a 1-l stainless steel autoclave was placed a filtrate containing 100 g/l of potassium, 50 g/l of methionine and 20 g/l of methionine dimer, and the filtrate was heated at 180° C. for 2 hours. After being cooled, the filtrate was taken out and an equal weight of isopropyl alcohol was added to the filtrate. The resulting liquid mixture was kept at 10° C. in a vessel and carbon dioxide gas was fed into the vessel until the liquid mixture was saturated with carbon dioxide gas under a pressure of 3 kg/cm$^2$ in terms of gauge pressure. The pH of the liquid mixture reached 8, and it was found that almost all of the crystals thus deposited were those of methionine and potassium bicarbonate. The filtrate left behind the removal of these deposited crystals had concentrations of potassium, methionine and methionine dimer of 6 g/l, 7 g/l and 2 g/l, respectively.

COMPARATIVE EXAMPLE 1

The same procedure as in Example 4 was repeated without the heat treatment of the filtrate. The filtrate left behind the removal of the deposited crystals had concentrations of potassium, methionine and methionine dimer of 6 g/l, 7 g/l and 10 g/l, respectively.

EXAMPLE 5

In a 1-l stainless steel autoclave was placed a filtrate containing 145 g/l/ of potassium, 50 g/l of methionine and 20 g/l of methionine dimer, and the filtrate was heated at 180° C. for 1 hour. After being cooled, the filtrate was taken out and then concentrated to about 55% of the original weight. Then 40% by weight, relative to the concentrated filtrate, of isopropyl alcohol was added thereto. The resulting liquid mixture Afi was kept at 10° C. in a vessel, and carbon dioxide gas was fed into the vessel until the liquid mixture was saturated with carbon dioxide gas under a pressure of 3 kg/cm$^2$ in terms of gauge pressure. The pH of the liquid mixture reached 8 and it was found that almost all of the crystals thus deposited were those of methionine and potassium bicarbonate. The filtrate left behind the removal of these deposited crystals had concentrations of potassium, methionine and methionine dimer of 5 g/l, 2 g/l and 2 g/l, respectively.

COMPARATIVE EXAMPLE 2

The same procedure as in Example 5 was repeated without the heat treatment of the filtrate. The filtrate left behind the removal of the deposited crystals had concentrations of potassium, methionine and methionine dimer of 6 g/l, 3 g/l and 4 g/l, respectively.

What is claimed is:

1. A process for producing methionine which comprises the steps of:
   (A) adding at least one compound selected from potassium carbonate, potassium bicarbonate and potassium hydroxide to a solution containing 5-(β-methylmercaptoethyl)hydantoin to hydrolyze the 5-(β-methylmercaptoethyl)hydantoin to obtain a solution containing methionine,
   (B) saturating the solution containing methionine with carbon dioxide gas to deposit the methionine, and separating the deposited methionine while leaving a first filtrate behind,
   (C) dividing the first filtrate into a first part and a second part, returning the first part to step (A), and transferring the second part to step (D), wherein the first part of the first filtrate can be absent,
   (D) heating the second part of the first filtrate to obtain a heat-treated filtrate, adding a water-miscible solvent to the heat-treated filtrate and saturating the heat-treated filtrate with carbon dioxide gas to deposit the methionine and potassium bicarbonate, and separating the deposited methionine and potassium bicarbonate while leaving a second filtrate behind, and
   (E) discharging the second filtrate or returning it to step (A).

2. The process of claim 1, wherein in step (D) the second part of the first filtrate is heated at an approximate temperature of from 150° to 200° C.

3. The process of claim 1, wherein in step (D) the second part of the first filtrate is heated for an approximate period of from 0.3 to 10 hours.

4. The process of claim 1, wherein the water-miscible solvent in step (D) is at least one member selected from the group consisting of isopropyl alcohol, methanol and acetone.

5. The process of claim 1, wherein in step (D) the water-miscible solvent is added to the heat-treated filtrate in an amount of from 0.2 to 2 parts by weight per part by weight of the heat-treated filtrate.

6. The process of any one of claim 1, wherein the step of saturating the heat-treated filtrate with carbon dioxide gas in step (D) is finished at an approximate temperature of from −10° to +40° C.

7. The process of claim 1, wherein in step (D) the heat-treated filtrate is saturated with carbon dioxide gas by compressing the gas under an approximate gauge pressure of from 0.5 to 20 kg/cm$^2$G.

* * * * *